United States Patent [19]

Forand et al.

[11] 4,418,151

[45] Nov. 29, 1983

[54] ASSAY PROCESS WITH NON-BOILING DENATURATION

[75] Inventors: Ronald R. Forand, Maynard; Edward T. Menz, Jr., Quincy, both of Mass.

[73] Assignee: Rohm and Haas Company, Philadelphia, Pa.

[21] Appl. No.: 248,826

[22] Filed: Mar. 30, 1981

[51] Int. Cl.$^3$ .................. G01N 33/36; G01N 33/60
[52] U.S. Cl. .................. 436/505; 436/804; 436/825
[58] Field of Search .................. 424/1, 12; 23/230 B; 436/505, 804, 825

[56] References Cited

U.S. PATENT DOCUMENTS

| | | |
|---|---|---|
| 3,591,678 | 7/1971 | Ellenbogen et al. . |
| 3,937,799 | 2/1976 | Lewin et al. . |
| 3,952,091 | 4/1976 | Grunberg et al. . |
| 3,972,991 | 8/1976 | Caston et al. . |
| 3,981,863 | 9/1976 | Niswender et al. . |
| 4,028,465 | 6/1977 | Lewin et al. . |
| 4,188,189 | 2/1980 | Allen . |

OTHER PUBLICATIONS van de Wiel, Nuclear Science Abstracts, vol. 33: Abstract #12479 (1976).
Biochim. Biophys. Acta, 158 (1968) 292-295, "A Procedure for Detaching Bound Vitamin $B_{12}$ from its transport proteins", Ralph Gräsbeck et al.
Biochim. Biophys. Acta, 343 (1974) 627-631, "Effect of pH on Vitamin $B_{12}$ Binding by Transcobalamins", Peter Newmark & Sylvia Mester.
Clinical Chemistry, vol. 22, No. 5 (1976) 647-649, "Decreased Radioassay Values for Folate After Serum Extraction When Pteroylglutaxic Acid Standards are Used" (Author: Gary A. Mitchell et al.).
Clinical Chemistry, vol. 26, No. 2 (1980) 323-326, "Room Temperature Radioassay for $B_{12}$ with Oyster Toadfish (Opsanus tau) Serum as Binder", Dianyssis S. Ithakissios.
Clinical Chemistry, vol. 27, No. 2 (1981) 263-267, "Radioassay for Cotalamin (Vit.$B_{12}$) Requiring No Pretreatment of Serum", Thomas M. Houts et al.
Allen and Mehlman, "Isolation of Gastric Vitamin $B_{12}$-Binding and Proteins Using Affinity Chromatography I. Purification and Properties of Human Intrinsic Factor", J. Bio. Chem. 248: 3660-3669 (1973).
Allen and Hehlman, "Isolation of Gastric Vitamin $B_{12}$--Binding and Proteins Using Affinity Chromatography, I. Purification and Properties of Hog Intrinsic Factor and Hog Non-Intrinsic Factor," J. Biol. Chem., 248: 3670-3680 (1973).
Kon, "Other Factors Related to Vitamin $B_{12}$" Biochem. Soc. Smp. (Cambridge, Engl.) 13: 17-35 (1953).
Ford et al., "The Occurrence of Cyanocobalamin and Related Compounds in Natural Materials," Proc. Nutr. Soc., 12: xi-xii (1953).
Glase, "Gastric Intrinsic Factor and Other Vitamin $B_{12}$ Binders, Biochemistry, Physiology, Pathology and Relation to Vitamin $B_{12}$ Metabolism," George Thieme Publishers Stuttgart (1974), p. 96.
Allen, "Plasma Transport of Vitamin $B_{12}$, Vitamin $B_{12}$ Analogues" (Info. fr. Jap. Pat. Abstract).
Rothenberg, "In Vitro Radioistopic Methods for Clinical Evaluation of Vitamin $B_{12}$ and Folic Acid Metabolism" In Vitro Radioisotopic Methods; and Progress in Analytical Chemistry" 1, pp. 77-96, Ewings Simmons (1974).

*Primary Examiner*—Christine M. Nucker
*Attorney, Agent, or Firm*—Terence P. Strobaugh

[57] ABSTRACT

Competitive protein binding radioassay for sera (or cell) vitamin $B_{12}$ and/or serum folate (target components, or analytes) or other target components in liquid ambient utilizing a highly alkaline (pH 12-14) environment and reducing agent for denaturing separating the target component(s) from serum without boiling, consistent with other requirements of such assays, then reducing pH to an 8-10 range for effecting the competitive protein binding after which protein bound and unbound groups of radioactively tagged replicates of the target component(s) can be separated and detected to determine content of the target component(s) in the original serum (or cell), i.e. original endogenous analyte(s).

10 Claims, 4 Drawing Figures

ASSAY PROCESS WITH NON-BOILING DENATURATION

BACKGROUND OF THE INVENTION

The present invention relates to clinical assay processes utilizing denaturation (conversion of endogenous material to an assayable form) and more particularly to processes for determination of human sera and cell levels of vitamin $B_{12}$ and/or folate by radioassay without use of boiling for denaturation. The invention may also be applied to other target components (analytes) of sera or cells (endogenous content) and to other forms of assay.

Measurement of the concentration of folate and vitamin $B_{12}$ in the serum and of folate in red blood cells, is useful as an adjunct in the clinical diagnosis and differentation of various types of nutritional anemia. Deficiencies in these vitamins predominantly arise from either inadequate diet, malabsorption, or alcoholism.

Deficiency in vitamin $B_{12}$ may result in neurological damage. Further, as this vitamin is necessary to transport N-methyltetrahydrofolate across human cell walls, its absence may also disturb folate metabolism and result in megaloblastic anemias. As megaloblastosis may also be produced by folate deficiency due to other causes, it is necessary to determine if it is caused by a deficiency of either or both vitamins.

Before the advent of radioassay procedures, microbiological assays were the principal means of determining the levels of serum folate and vitamin $B_{12}$. Such assays are time consuming and are subject to errors from the other factors that may influence growth rate such as presence of antibiotics and antimetabolites in the sample.

Following the development of the general features of saturation analysis or competitive protein binding (CPB) radioassay, and of specific radioassays for folate and vitamin $B_{12}$, microbiological assays have been largely replaced. The radioassay techniques not only produced results from correlated well with microbiological values, but also often provided better precision and freedom from interferences at lower costs of time and money. The principle of competitive binding used in these radioassays involves binding of analytes and tagged analogs thereof to a fixed quantity of a material, generally a protein, that has binding sites that are specific for the analytes and analogs. For vitamin $B_{12}$, purified intrinsic factor (e.g. using hog intrinsic factor, human IF, chicken or toad fish sera) is used as a binding protein; for folate assays, the folate binding protein in β-lactoglobulin is used. The competition for a limited number of binding sites of the specific protein occurs between the analyte present in the sample or standard and a small fixed quantity of a tracer (an analog of the analyte that has been labeled with a radioisotope). When there is zero endogenous analyte present, the tracer has no competition and occupies all of the sites of the binding protein. Separation of the bound and unbound (free) fractions of tracer, followed by measurement of one of these fractions permits one to construct a standard curve of the amount of radioactivity as a function of the concentration of analyte. Amounts of analyte in unknown samples can be read from the standard curve using radioactivity readings of such samples.

It is an important object of the present invention to provide improved assay processes of the class described.

SUMMARY OF THE INVENTION

The invention is broadly applicable to various forms of assay for various analytes, but for illustrative purposes is initially summarized with respect to radioassay of vitamin $B_{12}$ and/or folate.

A radioassay process for analysis of target components of sera utilizing competitive protein binding and comprising the steps of:

(a) contacting a precise amount of serum sample having one or more endogenous target components with liquid medium containing a reducing agent and radioactively tagged replication(s) of the target components(s) and incubating substantially at room temperature to initiate denaturation (irreversible separation) of the target component(s) from endogenous binder protein(s) in the serum, (b) providing additional liquid medium containing a means of establishing a pH in the medium of at substantially 12.0–14.0 and incubating substantially at ambient temperature to complete the denaturation (irreversible separation) of the target component(s) from endogenous binder protein(s) in the serum, (c) reducing the pH to lower range(s) suitable for target component binding, (d) providing, simultaneously with the separation or thereafter, new binding protein(s) of the target component(s), (e) incubating to establish binding of target component(s) and tagged replications to the new binding protein(s), and (f) separating unbound tagged replicates from protein bound replicates as separate groups and measuring radioactive emission from one or both groups to provide a count correlatable with the competitive binding result and with target component(s) content of the original serum.

A measured amount of serum is mixed with a constant amount of radioactivity tagged, vitamin $B_{12}$ and/or folate tracer in an aqueous solution. The solution is exposed to a mercaptan denaturing agent in the presence of a conversion agent, e.g. potassium cyanide providing useful cyano-group linkages for the vitamin $B_{12}$ and its replicates. In this process, the serum binding proteins are irreversibly denatured and both vitamin $B_{12}$ and folate are released. This denaturation and release step is at pH 12–14, preferably 12–13. A preferred and distinctly advantageous mercaptan denaturing agent is dithiotetritol. The utilization of such agents and pH levels affords denaturation without boiling in separating these (and other) analytes from endogenous binders and useful benefits in converting the radioactivity tagged analogs or replicates of the analytes into useful form for assay procedures.

Apart from vitamin $B_{12}$ and/or folate, the invention can be utilized in radioassays e.g. for other stable vitamins or other analytes which can withstand highly alkaline conditions used in denaturation. Apart from CPB the invention can be used in antibody differentiating assays. The tracer method can rely on, e.g., fluorescence rather than radioactivity. Still further variations will be apparent to those skilled in the art.

Volumes of reagents, patient samples, standards and denaturing agent should be controlled to most effectively utilize the non-boiling benefits of the present invention.

The mercaptan reducing agent is preferably a form of dithiotetritol and more particularly and with distinct advantage dithiothreitol (threo -1,4 dimercapto-2,3 butane diol).

After the addition of binding proteins, a complex is formed between the analyte and its respective binding proteins. This binding step takes place at pH 8–10, preferably 9.3. Subsequent steps are then carried out under usual CPB radioassay conditions. Following an incubation, the bound and unbound fractions of the analyte and tracer are separated by absorption and a standard curve can be made. The radioactivity of the bound and/or unbound vitamin $B_{12}$ and/or folate (supernate) can then be counted and plotted on the standard curve.

Other objects, features and advantages will occur from the following description of preferred embodiments, made with reference to the accompanying drawing in which:

DETAILED DESCRIPTION OF PREFERRED EMBODIMENTS

Figure 1:
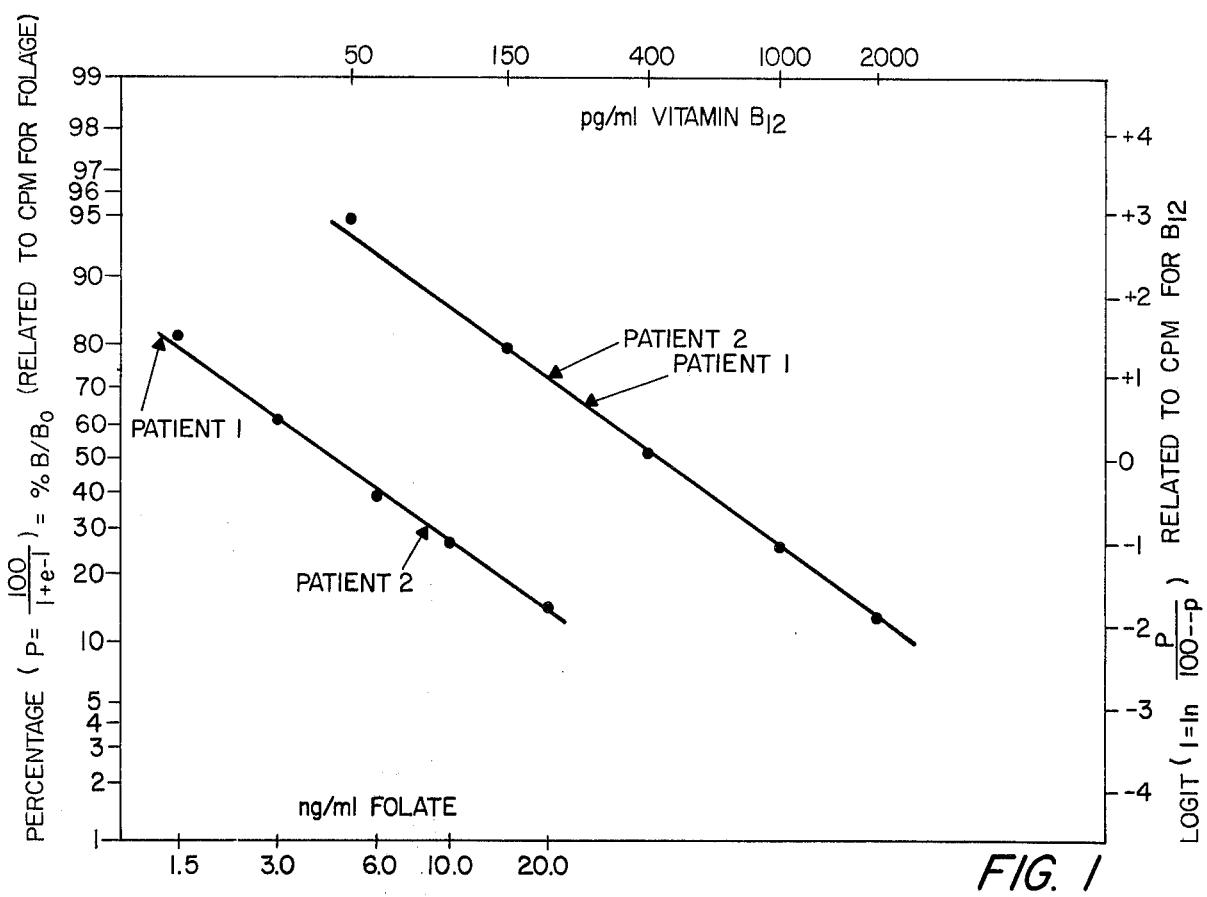
FIGS. 1–2 are examplary "standard" curves obtained in practice of the invention.

Reagents typically used in practice of the radioassay process of the invention may comprise:

| | |
|---|---|
| ZERO STANDARD | Polymer base containing buffer and sodium azide. |
| VITAMIN STANDARD | Reconstituted standards contain vitamin $B_{12}$ (cyanocobalamin) and folate (N—methyltetrahydrofolate) as indicated below, in a polymer base containing buffer and sodium azide. |

| Vitamin $B_{12}$ pg/ml | Folate ng/ml |
|---|---|
| 50 | 1.5 |
| 150 | 3.0 |
| 400 | 6.0 |
| 1000 | 10.0 |
| 2000 | 20.0 |

| | |
|---|---|
| REDUCING AGENT | Aqueous solution of dithiothreitol (0.26 molar - |

| | |
|---|---|
| | 40 grams/liter). |
| EXTRACTANT | Sodium hydroxide and 0.01% potassium cyanide in water. |
| TRACER | Contains less than 1.5 μCi of 57-Co cyanocabalamin, and less than 3.0 μCi of 125-I folate in borate buffer containing sodium chloride, indicator dye, and sodium azide. Cobalamin specific activity is 2 Ci/μmole. [A portion of the extractant and of the tracer are mixed - freshly before each assay typically 100 microliters of each) - to produce a master tracer reagent.] |
| BLANK REAGENT | Borate-phosphate buffer with protein and sodium azide. |
| BINDER | Purified intrinsic factor and β-lactoglobulin in borate-phosphate buffer with protein and sodium azide. |
| ADSORBENT | Tablets of charcoal, polymer, binder and disintegrant or slurry of polymer coated charcoal and sodium azide in water. |

Sample preparation is done according to conventional radioassay practice for isolating transportable, storable (frozen) monoglutamate (maintenance nutrition requirement) species.

Reagent reconstitution from storage to use form involves distilled water addition (two milliliters added to each reagent (when the reagents per se are in 10–100 ml vials). The ultimate best proportioning is a ratio volume units of serum (s) to volume units of tracer (t) to volume units of extractant (e) of:

$$s:t: e = 2:2:1$$

The procedure for assay comprises establishing eighteen (nine sets of two) tubes (for one patient; adding tubes 19/20 for patient #2, 21/22 for #3, etc.) allocated as ¾ non-specific binding references shown in TABLE 1 below:

TABLE 1

FLOW SHEET FOR NO-BOIL COMBOSTAT PROCEDURE

| Tube No. | Purpose | Standard/ Sample μl | Master Tracer Reagent μl | Extractant μl | | Binder μl | Blank Reagent μl | | Tablet (Slurry) | |
|---|---|---|---|---|---|---|---|---|---|---|
| 1,2 | Total Count | — | 200 | Vortex, then | 100 | Vortex | — | 1000 | Vortex | — | Vortex for 10 sec. |
| 3,4 | Blank | 200* | 200 | Incubate | 100 | Incubate | — | 1000 | Incubate | 1 | Incubate |
| 5,6 | Zero Std. | 200 | 200 | for | 100 | for | 1000 | — | for | 1 | for |
| 7,8 | 1.5/50 Std. | 200 | 200 | 15 | 100 | 5 | 1000 | — | 20 | 1 | 20 |
| 9,10 | 3.0/150 Std. | 200 | 200 | minutes | 100 | minutes | 1000 | — | minutes | 1 | minutes |
| 11,12 | 6.0/400 Std. | 200 | 200 | at | 100 | at | 1000 | — | at | 1 | |
| 13,14 | 10.0/1000 Std. | 200 | 200 | R.T. | 100 | R.T. | 100 | — | R.T. | 1 | Centrifuge for 10 minutes |
| 15,16 | 20.0/2000 Std. | 200 | 200 | in the | 100 | in the | 1000 | — | in the | 1 | Decant |
| 17,18 etc. | Patient #1 | 200 | 200 | dark | 100 | dark | 1000 | — | dark | 1 | Count Supernates. |

*200 μl Zero Standard

TABLE 1 (see Page 6A below)

Table 1 also indicates the steps applied to each tube set, i.e. pipetting 200 micro-liters of standard into tubes 3-18+ and 200 micro-liters of master tracer reagent(s) into tubes 1-18+, vortex mixing (for 1-2) seconds and incubation, pipetting 100 micro-liters of extractant into all the tubes, repeating vortex mix and incubation steps, adding one milliliter blank reagent to 1-4 and one milliliter of binder to 3-18+, vortex mix and incubation again, then adding tablet or slurry to tubes 3-18+, repeating vortex mix and incubation and then centrifugation of all tubes, decanting supernate (i.e. liquid) out of tubes 3-18+ leaving solids (tablet or powder) behind. The supernate is moved to new tubes, i.e. 3A, 4A, 5A, 6A, etc., which can be used for gamma count testing. The gamma counter is adjusted to assure less than 3% of crossover between 57-cobalt and 125-iodine readings.

Figure 2:
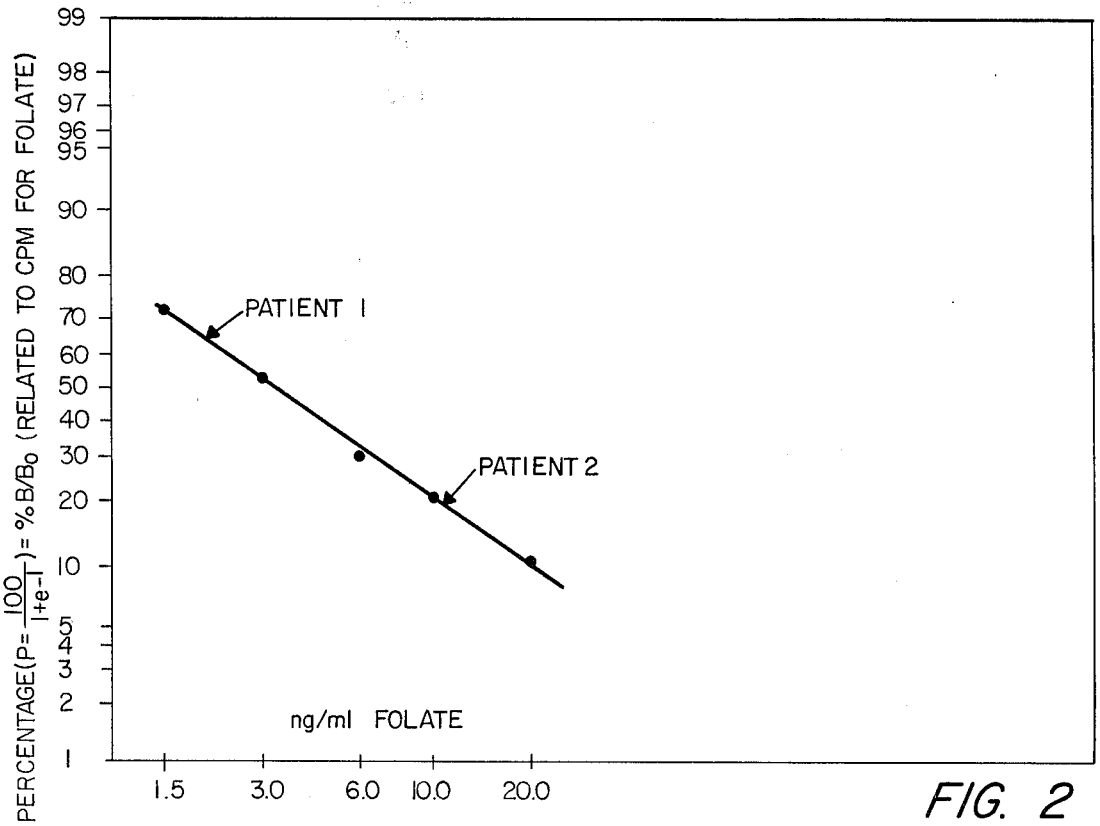

FIG. 1 shows typical results for utilization of the above process with a lower standard curve for folate (left ordinate and lower abcissa) and upper curve for $B_{12}$ (right ordinate and upper abcissa). Points are plotted using abcissa values of the standards and corresponding ordinate derivations of their CPM readings. The standard curves are plotted from these points. Then patient CPM's can be inserted, traced over from their ordinate values and read off as weight per volume (ng or pg per ml) values on the respective abcissas. The foregoing applies to serum. FIG. 2 is a similar standard curve for folate testing above with a variation in tracer and master reagent from the FIG. 1 conditions. Red cell readings are subject to the further folate correction that $$RCF = (100\% \times D \times C)/H$$

where RCF is red cell folate concentration (ng/ml), C is ng/ml of hemolysate aliquot analyzed, H is percentage hematocrit, D is the applicable dilution factor (41 in conventional practice).

Figure 3:
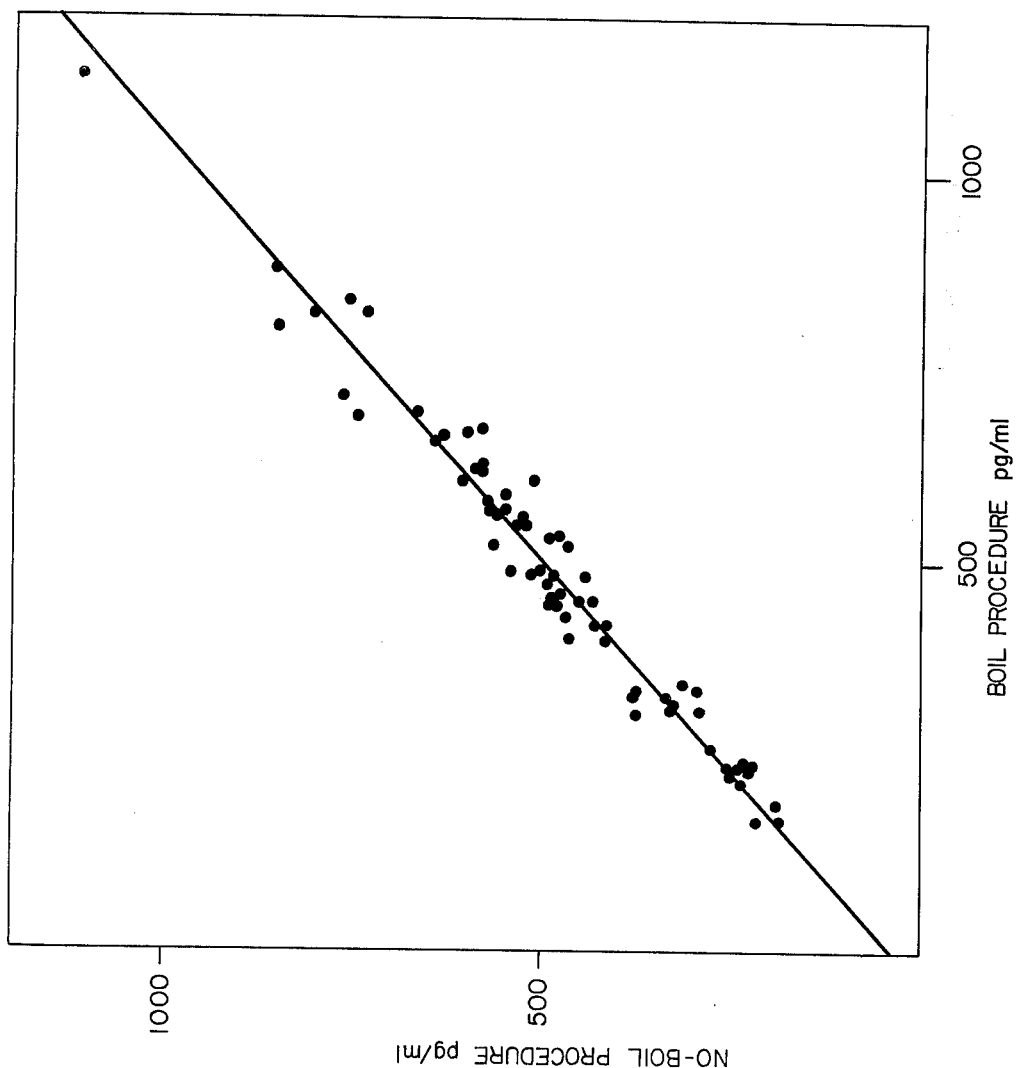
FIGS. 3–4 are correlations of $B_{12}$ and folate results, respectively, through the present invention with conventional radioassay results.
Figure 4:
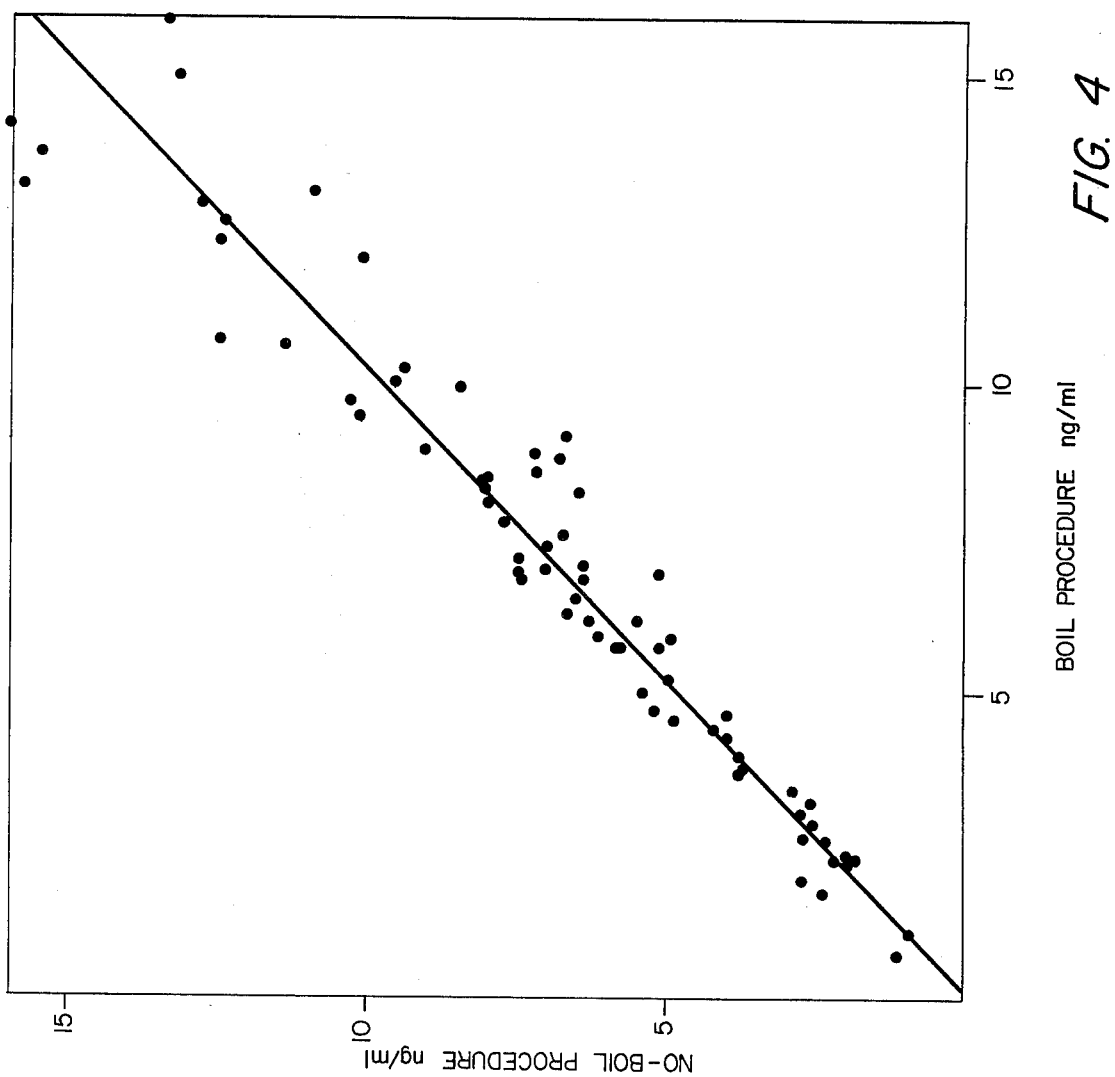

FIGS. 3 and 4 correlate the $B_{12}$ and folate (respectively) concentrations determined through use of the above described process (no boil denaturation) of the present invention and prior art boiling denaturation processes. Inner medians are drawn through the points plotted and reliable correlation is apparent.

It is evident that those skilled in the art, once given the benefit of the foregoing disclosure, may now make numerous other uses and modifications of, and departures from the specific embodiments described herein without departing from the inventive concepts. Consequently, the invention is to be construed as embracing each and every novel feature and novel combination of features present in, or possessed by, the apparatus and techniques herein disclosed and limited solely by the scope and spirit of the appended claims.

What is claimed is:

1. A radioassay process for analysis of the target components folate or Vitamin $B_{12}$ and folate utilizing competitive protein binding which comprises the steps of:
   (a) contacting a precise amount of serum sample having folate or Vitaming $B_{12}$ and folate endogenous target components with liquid medium containing a mercaptan reducing agent and radioactively tagged replication(s) of folate or Vitamin $B_{12}$ and folate target component(s) and incubating substantially at room temperature to initiate denaturation (irreversible separation) of the target component(s) from endogenous binder protein(s) in the serum,
   (b) providing additional liquid medium containing a means of establishing a pH in the medium at substantially 12.0-14.0 and incubating at substantially ambient temperature to complete the denaturation of the target component(s) from endogenous binder protein(s) in the serum,
   (c) reducing the pH to 8-10,
   (d) adding simultaneously with the separation or thereafter, binding protein(s) of the target component(s),
   (e) incubating to establish binding of target component(s) and tagged replications to the binding protein(s), and
   (f) separating unbound tagged replicates from protein bound replicates as separate groups and measuring radioactive emission from one or both groups to provide a count correlatable with the competitive binding result and with target component(s) content of the original serum.

2. The radioassay process in accordance with claim 1 wherein the mercaptan reducing agent comprises dithiotetritol.

3. The radioassay process in accordance with claim 1 or 2 wherein the target component comprises folate.

4. The radioassay process in accordance with claim 3 wherein the tagged replicate comprises a folate derivative tagged with iodine-125 and the binding protein comprises purified beta-lactoglobulin.

5. The radioassay process in accordance with claim 1 or 2 wherein the target components comprise vitamin $B_{12}$ and folate.

6. The radioassay process in accordance with claim 5 wherein the tagged replicate comprises Vitamin $B_{12}$ tagged with cobalt-57 and folate tagged with iodine-125 the proteins are purified intrinsic factor and purified beta-lactoglobulin, respectively and a buffer admixed therein to establish a pH of 8-10.

7. The radioassay process in accordance with claim 2 wherein the reduction at 12-14 pH is in the presence of potassium cyanide.

8. A radioassay process wherein the target components comprise folate and vitamin $B_{12}$ for assay, the tagged replicates comprise folate derivative tagged with iodine-125 and Vitamin $B_{12}$ tagged with cobalt-57 and the binding protein comprises beta-lactoglobulin and purified intrinsic factor respectively and buffer admixed therewith to establish a pH of 8-10 wherein radioemissions from both tagged replicates are separated based on differing energy levels.

9. A radioassay process for analysis of Vitamin $B_{12}$ utilizing competitive protein binding which comprises:
   (a) contacting a precise amount of serum sample containing Vitamin $B_{12}$ with liquid medium containing a mercaptan reducing agent radioactively tagged Vitamin $B_{12}$ and incubating at substantially room temperature to initiate denaturation of the Vitamin $B_{12}$ from endogenous binder proteins in the serum,
   (b) providing additional liquid medium containing a means of establishing a pH in the medium of substantially 12.0-14.0 and incubating substantially at ambient temperature to complete the denaturation,
   (c) reducing the pH to 8-10,
   (d) adding, simultaneously with the separation or thereafter, purified intrinsic factor,
   (e) incubating to establish binding of Vitamin $B_{12}$ and tagged Vitamin $B_{12}$ replications to the purified intrinsic factor, and
   (f) separating unbound tagged Vitamin $B_{12}$ replicates from protein bound Vitamin $B_{12}$ as separate groups and measuring radioactive emission to provide a count correlatable with the competitive binding result and with Vitamin $B_{12}$ content of the original serum.

10. The radioassay process in accordance with claim 9 wherein the reducing agent is dithiotetritol.

* * * * *

UNITED STATES PATENT AND TRADEMARK OFFICE
CERTIFICATE OF CORRECTION

PATENT NO. : 4,418,151

DATED : November 29, 1983

INVENTOR(S) : Ronald R. Forand and Edward T. Menz, Jr.

It is certified that error appears in the above—identified patent and that said Letters Patent is hereby corrected as shown below:

Name of Assignee "Rohm and Haas Company" should read

--Micromedic Systems, Inc.--.

*Signed and Sealed this*

*Twenty-seventh* Day of *March 1984*

[SEAL]

*Attest:*

GERALD J. MOSSINGHOFF

*Attesting Officer*     *Commissioner of Patents and Trademarks*